US011267944B2

(12) United States Patent
Liu et al.

(10) Patent No.: US 11,267,944 B2
(45) Date of Patent: Mar. 8, 2022

(54) RADIATION CURABLE ARTICLE AND METHOD FOR MAKING AND USING SAME

(71) Applicant: SAINT-GOBAIN PERFORMANCE PLASTICS CORPORATION, Solon, OH (US)

(72) Inventors: Xipeng Liu, Concord, MA (US); Michael J. Tzivanis, Chicopee, MA (US); Jianfeng Zhang, Shrewsbury, MA (US)

(73) Assignee: SAINT-GOBAIN PERFORMANCE PLASTICS CORPORATION, Solon, OH (US)

( * ) Notice: Subject to any disclaimer, the term of this patent is extended or adjusted under 35 U.S.C. 154(b) by 0 days.

(21) Appl. No.: 15/395,381

(22) Filed: Dec. 30, 2016

(65) Prior Publication Data

US 2017/0190859 A1    Jul. 6, 2017

Related U.S. Application Data

(60) Provisional application No. 62/273,120, filed on Dec. 30, 2015.

(51) Int. Cl.
| | |
|---|---|
| *C08J 7/12* | (2006.01) |
| *B29C 64/124* | (2017.01) |
| *C08K 5/56* | (2006.01) |
| *B33Y 80/00* | (2015.01) |
| *A61L 31/06* | (2006.01) |
| *B29C 35/08* | (2006.01) |
| *C09J 183/14* | (2006.01) |
| *C08G 77/12* | (2006.01) |
| *C08G 77/20* | (2006.01) |
| *B33Y 10/00* | (2015.01) |
| *B33Y 70/00* | (2020.01) |
| *B29K 83/00* | (2006.01) |
| *B29K 105/00* | (2006.01) |

(52) U.S. Cl.
CPC .............. *C08J 7/123* (2013.01); *A61L 31/06* (2013.01); *B29C 35/0805* (2013.01); *B29C 64/124* (2017.08); *B33Y 80/00* (2014.12); *C08K 5/56* (2013.01); *C09J 183/14* (2013.01); *B29C 2035/0822* (2013.01); *B29C 2035/0827* (2013.01); *B29C 2035/0833* (2013.01); *B29K 2083/00* (2013.01); *B29K 2105/0058* (2013.01); *B33Y 10/00* (2014.12); *B33Y 70/00* (2014.12); *C08G 77/12* (2013.01); *C08G 77/20* (2013.01); *C08J 2383/14* (2013.01)

(58) Field of Classification Search
CPC ...... C08J 7/123; C08J 2383/14; C09J 183/14; B29C 35/0808; B29C 2035/0833; B29C 2035/0822; B29C 64/112; B29C 2035/0827; A61L 31/06; B33Y 70/00; B33Y 80/00; B33Y 10/00; B29K 2083/00; B29K 2105/005

See application file for complete search history.

(56) References Cited

U.S. PATENT DOCUMENTS

| | | | |
|---|---|---|---|
| 5,366,806 A | * | 11/1994 | Fujiki .................. C08F 291/00 428/412 |
| 5,639,413 A | | 6/1997 | Crivello |
| 6,620,569 B2 | | 9/2003 | Tsubuko et al. |
| 7,307,123 B2 | | 12/2007 | Johnson et al. |
| 7,833,577 B2 | | 11/2010 | Sheridan et al. |
| 8,097,689 B2 | | 1/2012 | Ahn et al. |
| 8,198,357 B2 | | 6/2012 | Jeram et al. |
| 8,232,363 B2 | | 7/2012 | Hu et al. |
| 8,334,037 B2 | | 12/2012 | Sheridan et al. |
| 8,673,419 B2 | | 3/2014 | Determan et al. |
| 8,871,861 B2 | | 10/2014 | Shoshi et al. |
| 8,952,118 B2 | | 2/2015 | Arkles et al. |
| 9,205,601 B2 | | 12/2015 | Desimone et al. |
| 9,216,546 B2 | | 12/2015 | Desimone et al. |
| 9,216,547 B2 | | 12/2015 | Elsey |
| 9,228,117 B2 | | 1/2016 | Sherman et al. |
| 2007/0049716 A1 | | 3/2007 | Sayre |
| 2007/0148409 A1 | | 6/2007 | Rios et al. |
| 2007/0208132 A1 | | 9/2007 | Geisberger et al. |
| 2007/0244287 A1 | | 10/2007 | Hatanaka et al. |
| 2008/0027163 A1 | | 1/2008 | McNulty et al. |
| 2008/0033071 A1 | | 2/2008 | Irmer et al. |

(Continued)

FOREIGN PATENT DOCUMENTS

| | | |
|---|---|---|
| AU | 2008343078 B2 | 7/2009 |
| AU | 2013204631 B2 | 5/2013 |
| CN | 101029176 A | 9/2007 |
| CN | 104140533 A | 11/2014 |
| CN | 104559196 A | 4/2015 |

(Continued)

OTHER PUBLICATIONS

International Search Report for PCT/US2016/069436, International Searching Authority, dated Apr. 14, 2017.

(Continued)

*Primary Examiner* — Jessica M Roswell
(74) *Attorney, Agent, or Firm* — Abel Schillinger, LLP; Chi Suk Kim

(57) ABSTRACT

A radiation curable article includes a silicone composition including a silicone oligomer and a photoactive catalyst, wherein the silicone oligomer comprises at least one alkenyl group and at least one hydride group, the radiation curable silicone oligomer having a viscosity of less than about 100,000 centipoise prior to cure. Further included is a method of forming a radiation curable article includes providing a silicone composition including a silicone oligomer and a photoactive catalyst, wherein the silicone oligomer includes at least one alkenyl group and at least one hydride group, the silicone oligomer having a viscosity of less than about 100,000 centipoise prior to cure; and irradiating the silicone composition with a radiation source.

11 Claims, 1 Drawing Sheet

(56) References Cited

U.S. PATENT DOCUMENTS

| | | |
|---|---|---|
| 2008/0221232 A1 | 9/2008 | Ou et al. |
| 2009/0130449 A1 | 5/2009 | El-Siblani |
| 2010/0183814 A1 | 7/2010 | Rios et al. |
| 2010/0310805 A1 | 12/2010 | Ou et al. |
| 2012/0027970 A1 | 2/2012 | Irmer et al. |
| 2012/0070622 A1 | 3/2012 | Stocq |
| 2012/0245272 A1 | 9/2012 | Dent et al. |
| 2013/0341671 A1* | 12/2013 | Ona ................. H01L 33/56 257/100 |
| 2014/0322519 A1 | 10/2014 | Ahn et al. |
| 2015/0072293 A1 | 3/2015 | Desimone et al. |
| 2016/0059484 A1 | 3/2016 | Desimone et al. |
| 2016/0325493 A1 | 11/2016 | Desimone et al. |
| 2017/0283655 A1 | 10/2017 | Kenney et al. |

FOREIGN PATENT DOCUMENTS

| | | |
|---|---|---|
| WO | 2009145086 A1 | 12/2009 |
| WO | 2012145449 A1 | 10/2012 |
| WO | 2015020692 A1 | 2/2015 |
| WO | 2015061075 A1 | 4/2015 |
| WO | 2015080888 A2 | 6/2015 |
| WO | 2015105762 A1 | 7/2015 |
| WO | 2015142546 A1 | 9/2015 |
| WO | 2015164234 A1 | 10/2015 |
| WO | 2015164779 A1 | 10/2015 |
| WO | 2015195909 A1 | 12/2015 |
| WO | 2015195920 A1 | 12/2015 |
| WO | 2015195924 A1 | 12/2015 |
| WO | 2016044547 A1 | 3/2016 |

OTHER PUBLICATIONS

International Search Report for PCT/US2017/030183, International Searching Authority, dated Jun. 21, 2017.

Etienne Delebecq et al, "Looking over Liquid Silicone Rubbers: (1) Network Topology vs Chemical Formulations," ACS Applied Materials & Interfaces, vol. 4, No. 7, Jun. 21, 2012, pp. 3340-3352, XP055740450, US, ISSN: 1944-8244, DOI: 10.1021/am300502r.

Anonymous: "Momentive Introduces New Ultraviolet Curing Technology for Platinum Silicone Elastomers/Business Wire," Oct. 27, 2010, XP055740546, Retrieved from the Internet: URL:https://www.businesswire.com/news/home/20101027006097/en/Momentive-Introduces-New-Uitraviolet-Curing-Technology-for-Platinum-Silicone-Elastomers (retrieved on Oct. 15, 2020).

Anonymous: "Types of Silicone Molding/Medical," Feb. 15, 2018, XP055740551, Retrieved from the Internet: URL: https://www.medical.saint-gobain.com/blog/types-silicone-molding (retrieved on Oct. 15, 2020).

* cited by examiner

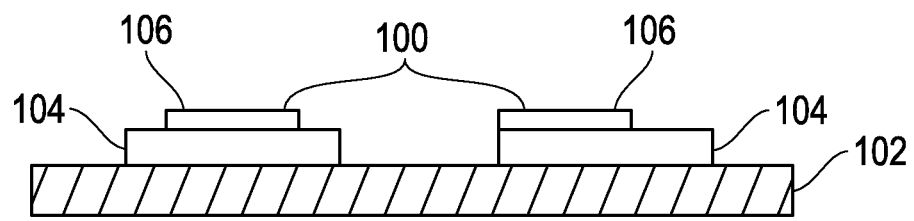

RADIATION CURABLE ARTICLE AND METHOD FOR MAKING AND USING SAME

CROSS-REFERENCE TO RELATED APPLICATION(S)

This application claims priority under 35 U.S.C. § 119(e) to U.S. Patent Application No. 62/273,120 entitled "RADIATION CURABLE ARTICLE AND METHOD FOR MAKING AND USING SAME," by Xipeng LIU, filed Dec. 30, 2015, which is assigned to the current assignee hereof and incorporated herein by reference in its entirety.

FIELD OF THE DISCLOSURE

The disclosure, generally, is related to a radiation curable article and method of forming the radiation curable article.

BACKGROUND

Curable silicone compositions are used in a variety of applications that range from the automotive industry to medical devices. Typical commercial formulations of silicone compositions include a multi-component mixture of a vinyl-containing polydiorganosiloxane, a hydrogen-containing polydiorganosiloxane, catalyst, and filler. Often, the commercial formulation is a two-part formulation that is mixed together prior to use. Once the commercial formulation is mixed, the silicone composition is subsequently molded or extruded and vulcanized.

In many cases, the silicone composition is used as a film, can be extruded into a profile, or injection molded within a mold cavity. The conventional silicone compositions typically have relatively high viscosity. Further, conventional silicone compositions are thermally cured at elevated temperatures. As a result, conventional silicone compositions are not desirable for new technology applications, such as three dimensional printing, where low viscosity of the polymer at room temperature for fast fluid delivery and speed of cure are desired.

As such, an improved silicone composition and method of forming articles including the improved silicone composition would be desirable.

SUMMARY

In an embodiment, a radiation curable article includes a silicone composition including a silicone oligomer and a photoactive catalyst, wherein the silicone oligomer includes at least one alkenyl group and at least one hydride group, the radiation curable silicone oligomer having a viscosity of less than about 100,000 centipoise prior to cure.

In another embodiment, a method of forming a radiation curable article includes providing a silicone composition including a silicone oligomer and a photoactive catalyst, wherein the silicone oligomer includes at least one alkenyl group and at least one hydride group, the silicone oligomer having a viscosity of less than about 100,000 centipoise prior to cure; and irradiating the silicone composition with a radiation source.

BRIEF DESCRIPTION OF THE DRAWINGS

The present disclosure may be better understood, and its numerous features and advantages made apparent to those skilled in the art by referencing the accompanying drawings.

FIG. 1 includes an illustration of a radiation cured article.

The use of the same reference symbols in different drawings indicates similar or identical items.

DETAILED DESCRIPTION

The following description in combination with the FIGURE is provided to assist in understanding the teachings disclosed herein. The following discussion focuses on specific implementations and embodiments of the teachings. This focus is provided to assist in describing the teachings and should not be interpreted as a limitation on the scope or applicability of the teachings.

As used herein, the terms "comprises," "comprising," "includes," "including," "has," "having" or any other variation thereof, are open-ended terms and should be interpreted to mean "including, but not limited to . . . ." These terms encompass the more restrictive terms "consisting essentially of" and "consisting of." In an embodiment, a method, article, or apparatus that comprises a list of features is not necessarily limited only to those features but may include other features not expressly listed or inherent to such method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" is employed to describe elements and components described herein. This is done merely for convenience and to give a general sense of the scope of the invention. This description should be read to include one or at least one and the singular also includes the plural, or vice versa, unless it is clear that it is meant otherwise. For example, when a single item is described herein, more than one item may be used in place of a single item. Similarly, where more than one item is described herein, a single item may be substituted for that more than one item.

Unless otherwise defined, all technical and scientific terms used herein have the same meaning as commonly understood by one of ordinary skill in the art to which this invention belongs. The materials, methods, and examples are illustrative only and not intended to be limiting. To the extent not described herein, many details regarding specific materials and processing acts are conventional and may be found in reference books and other sources within the structural arts and corresponding manufacturing arts. Unless indicated otherwise, all measurements are at about 25° C. For instance, values for viscosity are at 25° C., unless indicated otherwise.

The disclosure generally relates to a radiation curable article. The radiation curable article includes a silicone composition of a silicone oligomer and a photoactive catalyst. "Silicone oligomer" as used herein refers to a molecular complex that includes a number of silicone monomer units. The silicone oligomer has a desirable viscosity for applications such as 3-dimensional (3D) printing. Further, the inclusion of the photoactive catalyst provides an expedient method of curing the silicone oligomer to provide the formation of three dimensional articles of any desired shape.

In an embodiment, the silicone oligomer includes at least two functional groups. In a particular embodiment, the at least two functional groups include an at least one unsaturated, carbon functional group and an at least one hydride group. In an embodiment, the unsaturated, carbon functional group includes an alkenyl group, an alkynyl group, or combination thereof. In a more particular embodiment, the at least two functional groups are at least one alkenyl group and at least one hydride group. In embodiment, the at least one hydride group and the at least one alkenyl group are each present at any reasonable position on the silicone oligomer. For instance, the at least two functional groups can be positioned on the backbone of the silicone oligomer or on a pendant group that is chemically bound to the backbone of the silicone oligomer. In a particular embodiment, the at least one hydride group and the at least one alkenyl group are each at a terminal end of the silicone oligomer. For instance, the at least one hydride group is at a terminal end of the silicone oligomer and the at least one alkenyl group is at an opposite terminal end of the silicone oligomer. In an exemplary embodiment, the at least one hydride group and the at least one alkenyl group of a silicone oligomer do not crosslink when present on the same oligomer. In a particular embodiment, the at least one hydride group of the silicone oligomer crosslinks with an at least one alkenyl group of a respective silicone oligomer. As such, any number of silicone oligomers can crosslink via a hydride-to-alkenyl covalent linkage when exposed to a radiation source. In a particular embodiment, the at least one hydride group and at least one alkenyl group are present on the silicone oligomer in a ratio of about 1:2 to about 2:1. In a more particular embodiment, the at least one hydride group and at least one alkenyl group are present on the silicone oligomer in a ratio of about 1:1. In an embodiment, "at least one alkenyl group" includes any reasonable number of covalent linkages such as at least two alkenyl groups, or even at least three alkenyl groups. In an embodiment, "at least one hydride group" includes any reasonable number of covalent linkages such as at least two hydride groups, or even at least three hydride groups. Although the unsaturated, carbon functional group is primarily described as an alkenyl group, any unsaturated, carbon functional group is envisioned such as an alkenyl group, an alkynyl group, or combination thereof.

In a particular embodiment, the silicone oligomer has a viscosity of less than about 100,000 centipoise prior to cure, such as less than about 50,000 centipoise prior to cure. Advantageously, the silicone oligomer having the viscosity as described is liquid at room temperature (at about 25° C.). In a particular embodiment, the silicone oligomer may include a number of D repeating units of less than about 500, such as about 4 to about 500, or even about 4 to about 100. "D" units are typically defined as $R_2SiO_{2/2}$, where R is an alkenyl group, an alkynyl group, a hydride group, an alkyl group, an alkoxy group, a phenyl group, a halogenated alkyl group, or any combination thereof. In an embodiment, the alkenyl, alkyl, or alkoxy group includes a $C_{1-6}$ hydrocarbon group, such as a methyl, ethyl, or propyl group. In a particular embodiment, the alkenyl group is a vinyl group. In a particular embodiment, the alkyl group is a methyl group. In an embodiment, the halogenated alkyl group is fluorinated. In an embodiment, the D units are substantially free of an alkenyl group, a hydride group, or combination thereof. "Substantially free" as used herein refers to less than about 0.1 mole of the total moles of the silicone oligomer. It will be appreciated that the viscosity of the silicone composition can be within a range between any of the minimum and maximum values noted above. It will be appreciated that the number of D repeating units can be within a range between any of the minimum and maximum values noted above.

In an example, the silicone oligomer further includes other units such as $RSiO_{3/2}$ units ("T" units) and $R_3SiO_{1/2}$ ("M" units), wherein R is defined as above. In an embodiment, the M unit is at respective ends of the silicone oligomer and each end includes the alkenyl group and the hydride group, respectively. In another embodiment, the M unit is at respective ends of the silicone oligomer and each end includes the alkynyl group and the hydride group, respectively. Any number of units is envisioned with the proviso that the silicone oligomer has a viscosity of less than about 100,000 centipoise, such as less than about 50,000 centipoise as discussed.

The silicone oligomer may, for example, include polyalkylsiloxanes, such as silicone polymers formed of a precursor, such as dimethylsiloxane, diethylsiloxane, dipropylsiloxane, methylethylsiloxane, methylpropylsiloxane, or combinations thereof. In a particular embodiment, the polyalkylsiloxane includes a polydialkylsiloxane, such as polydimethylsiloxane (PDMS). In a particular embodiment, the polyalkylsiloxane is the hydride-containing and the vinyl-containing silicone oligomer within the silicone composition. In an embodiment, the silicone composition is substantially free of a silicone oligomer than contains only either a hydride group or an alkenyl group, i.e. does not contain both the hydride group and the alkenyl group. "Substantially free" as used herein refers to less than about 0.1 weight % of the total weight of the silicone composition. In an example, the silicone polymer is non-polar and is free of halide functional groups, such as chlorine and fluorine, and of phenyl functional groups. Alternatively, the silicone polymer may include halide functional groups or phenyl functional groups. For example, the silicone polymer may include fluorosilicone or phenylsilicone.

The silicone composition further includes a photoactive catalyst. Typically, the photoactive catalyst is present to initiate the crosslinking process. Any reasonable photoactive catalyst that can initiate crosslinking when exposed to a radiation source is envisioned. Typically, the photoactive catalyst is dependent upon the silicone oligomer. In an embodiment, the photoactive catalyst is a hydrosilylation reaction catalyst. In a particular embodiment, the catalytic reaction includes aliphatically unsaturated groups (i.e. alkenyl group) reacted with Si-bonded hydrogen (H) in order to convert the addition-crosslinkable silicone oligomer into an elastomeric state by formation of a network either via chemical bonding or polymer chain entanglement. In a more particular embodiment, the network formed by the crosslinking of silicone oligomers is non-linear.

For instance, an exemplary photoactive catalyst is an organometallic complex compound of a transition metal. In an embodiment, the photoactive catalyst includes platinum, rhodium, ruthenium, the like, or combinations thereof. In a particular embodiment, the photoactive catalyst includes platinum. Further, any reasonable optional catalyst may be used with the photoactive catalyst. In an embodiment, the optional catalyst may or may not initiate crosslinking when exposed to a radiation source. Exemplary optional catalysts may include peroxide, tin, or combinations thereof. Alternatively, the silicone composition further includes a peroxide catalyzed silicone material. In another example, the silicone composition may include a combination of a platinum catalyst and peroxide catalyst. In a particular embodiment, a peroxide catalyst is provided as a cross-linking agent. The use of a cross-linking agent increases the number of covalent bonds formed between respective silicone oligomers. For instance, the addition of a peroxide catalyst in combination with the platinum catalyst increases the shore A durometer of the final cured article compared to a final cured article including a platinum catalyst without a peroxide catalyst. In an embodiment, the silicone composition is substantially free of any catalyst that does not initiate crosslinking when exposed to a radiation source.

The silicone composition may further include an additive. Any reasonable additive is envisioned. Exemplary additives may include, individually or in combination, a vinyl polymer, a hydride, an adhesion promoter, a filler, an initiator, an inhibitor, a colorant, a pigment, a carrier material, or any combination thereof. In a particular embodiment, the filler is an inorganic filler such as, for example, fumed silica, precipitated silica, or combination thereof. In an embodiment, the material content of the silicone oligomer is present at an amount of at least about 60 weight %, such as at least about 70 weight %, such as at least about 80 weight %, or even at least about 90 weight %, based on the total weight of the silicone composition. In an embodiment, the additive is present at an amount of up to about 40% based on the total weight of the silicone composition. In an embodiment, the silicone composition is substantially free of any additional vinyl polymer, a hydride, or combination thereof. In some embodiments, the silicone composition consists essentially of the respective silicone oligomer and catalyst as described above. In an embodiment, the silicone composition consists essentially of the silicone oligomer, catalyst, and a filler. As used herein, the phrase "consists essentially of" used in connection with the silicone composition precludes the presence of non-silicone polymers that affect the basic and novel characteristics of the silicone composition, although, commonly used processing agents and additives may be used in the silicone composition.

The silicone composition may further include a conventional, commercially prepared silicone material. The commercially prepared silicone material typically includes components such as the silicone polymer, a catalyst, a filler, and optional additives. Any reasonable filler and additives are envisioned. The photoactive catalyst that is initiated by the radiation source may be added separately or may be included within the commercially prepared formulation.

In an embodiment, the silicone oligomer is cured via a radiation source. During cure, the at least one hydride group of the silicone oligomer crosslinks with an at least one alkenyl group of a respective silicone oligomer. The source of radiation energy can include any reasonable radiation energy source such as actinic radiation. In a particular embodiment, the radiation source is ultraviolet light. Any reasonable wavelength of ultraviolet light is envisioned. In a specific embodiment, the ultraviolet light is at a wavelength of about 10 nanometers to about 500 nanometers. Further, any number of applications of radiation energy may be applied with the same or different wavelengths, depending upon the material and the desired result. It will be appreciated that the wavelength can be within a range between any of the minimum and maximum values noted above. The method of irradiating the silicone composition will be further discussed below. In an embodiment, the silicone oligomer is cured via thermal source.

In an embodiment, the radiation curable article may be formed by any reasonable means. The method of forming the radiation curable article includes providing the silicone composition including the silicone oligomer and the photoactive catalyst and subsequently irradiating the silicone composition with the radiation source. In an example, the radiation curable article is formed via extrusion, injection molding, or coating. In an embodiment, the silicone composition is advantageous for forming a three dimensional article via a three dimensional printing system. Any three dimensional printing system is envisioned and includes, but is not limited to, stereolithography (SLA), digital light processing (DLP), continuous liquid interface production (CLIP), and paste extrusion.

In an embodiment, an extrusion system is envisioned. In a particular embodiment, the extrusion system is configured for three dimensional printing. The extrusion system may include a pumping system and can include any number of devices that can be utilized to form the radiation curable article. For example, the pumping system can include a pumping device such as a gear pump, a static mixer, an extruder, a die, a radiation cure device, a post-processing device, or any combination thereof. The extrusion system receives the silicone composition as described above.

Typically, the silicone composition is mixed and pumped, i.e. extruded, through a die of the extrusion system. Any reasonable mixing apparatus is envisioned. In an embodiment, the silicone composition does not require heating prior to extrusion. In an alternative embodiment, heat may be applied to the silicone composition to facilitate extrusion by further decreasing the viscosity of the silicone composition. For instance, any reasonable heating temperature for the components of the silicone composition may be used to provide a silicone composition that can flow from the pumping system and extruded through the die without degradation of the material. For instance, the temperature may be about 10° C. to about 110° C. It will be appreciated that the heating temperature can be within a range between any of the minimum and maximum values noted above.

In an embodiment, the silicone composition is deposited, such as through a die. Any reasonable shape of the die is envisioned depending upon the final dimensions desired for the final article. In a more particular embodiment, the silicone composition is deposited through a die on a print region surface. Any print region surface is envisioned, however, in an exemplary embodiment, a low tack print region surface is desired. As illustrated in FIG. 1, a radiation curable article 100 is a three dimensional article formed on a print region surface 102. The radiation curable article 100 includes a first layer 104 and a successive layer, i.e. second layer, 106. The first layer 104 is directly in contact with and bonds directly to the second layer 106. In an exemplary embodiment, the first layer 104 directly bonds to the second layer 106 without any intervening layer. Each layer is formed of the silicone composition. As seen in FIG. 1, providing the silicone composition includes depositing the first layer 104 of the silicone composition and depositing an additional and successive amount of the silicone composition, such as at least the second layer 106, to create a three dimensional shape.

Although illustrated as two layers, any number of layers is envisioned. For instance, the number of layers is dependent upon the final properties and dimensions desired for the radiation curable article. In a particular embodiment, the number of layers are provided to form a three dimensional article. The radiation curable article may further include other layers not formed of the silicone composition. Any reasonable method of providing any additional layer is envisioned and is dependent upon the material chosen. Additional layers include, for example, any non-silicone polymeric layer, a reinforcing layer, a primer layer, a metallic layer, and the like. Any thickness of the other layers may be envisioned.

In an embodiment, the silicone composition is radiation cured. In a particular embodiment, the radiation curing can occur after the silicone composition is deposited on the print region surface. In a more particular embodiment, each layer is successively cured after each layer is deposited and before the next successive layer is deposited. For instance, a first layer is deposited and then cured, a second layer is deposited and then cured, with the process repeating until the desired three dimensional radiation cured article is formed. Each layer can have any thickness envisioned. In an embodiment, each layer can have a thickness between about 0.1 um and about 500 um. Each layer may or may not have the same thickness. It will be appreciated that the thickness can be within a range between any of the minimum and maximum values noted above. Further, each layer may or may not have the same shape. For instance, each layer can have a varying shape to form a three dimensional printed article of varying complexity. In an embodiment, the thickness and shape of the layer depends upon the amount of silicone composition deposited.

The radiation curing provides a continuous process of forming the radiation curable article. In an embodiment, the radiation curing of the silicone composition can include subjecting the silicone composition to one or more radiation sources. In a particular embodiment, the radiation source is sufficient to substantially cure the silicone composition and provide a three dimensional radiation cured article. In a more particular embodiment, the radiation source provides instant penetration of the radiation into the silicone composition and curing of the silicone composition.

Any reasonable radiation source is envisioned such as actinic radiation. In an embodiment, the radiation source is ultraviolet light (UV). Any reasonable wavelength of ultraviolet light is envisioned. In a specific embodiment, the ultraviolet light is at a wavelength of about 10 nanometers to about 500 nanometers, such as a wavelength of about 200 nanometers to about 400 nanometers. Further, any number of applications of radiation energy may be applied with the same or different wavelengths. In an embodiment, the system for forming the radiation curable article can include one or more ovens (e.g. infrared (IR) ovens, air ovens), one or more baths (e.g. salt water baths), or a combination thereof, to cure the silicone composition. The one or more IR ovens can operate at a particular peak wavelength. In certain instances, the peak wavelength of a first IR oven can be different from the peak wavelength of a second IR oven. In an embodiment, the silicone composition can be subjected to a heat treatment for a specified period of time. In a particular embodiment, the silicone composition can be subjected to curing in a first IR oven for a first period of time and then subject to curing in a second IR oven for a second period of time that is different from the first period of time. In one particular embodiment, use is made of a short wavelength IR oven. By short wavelength, it is meant that the peak wavelength is below 4 microns, typically below 3 microns, such as within a range of approximately 0.6 to 2.0 microns, such as 0.8 to 1.8 microns. Generally medium and longer wavelength IR ovens are characterized by a peak wavelength on the order of 4 to 8 microns, or even higher. It will be appreciated that the wavelength can be within a range between any of the minimum and maximum values noted above.

The process of forming the radiation cured article may further include thermal treatment of the radiation curable article. Any temperature for thermal treatment is envisioned. In an embodiment, the source of radiation and the thermal treatment may occur concurrently, in sequence, or any combination thereof. In a particular embodiment, the source of radiation and thermal treatment occurs concurrently.

Although formation of the three-dimension article is described above with an extrusion method, any method of providing and forming the three dimensional radiation cured article is envisioned. Another exemplary method of three dimensional printing includes providing the silicone composition by filling at least a portion of a container with the silicone composition. The container can include the silicone composition and the radiation source can cure at least a portion of the silicone composition within the container. For instance, the silicone composition can be selectively irradiated such that a portion of the silicone composition in the container is cured. The radiation source can be configured to irradiate a desired thickness and a desired shape from any reasonable direction envisioned. In an example, a portion of the silicone composition at the topmost layer in the container is irradiated and cured to form a shape having a particular dimension. In an embodiment, the cured portion can then be positioned in any direction envisioned, such as elevated up or down, and a subsequent portion of the silicone composition can be irradiated to build upon the already cured portion. This method of positioning the cured portion and irradiating a subsequent portion of the silicone composition to build upon the already cured portion can be repeated any number of times to form a three dimensional radiation cured article.

Once formed, the radiation cured article can undergo one or more post processing operations. Any reasonable post processing operations are envisioned. For instance, the radiation cured article can be subjected to a post-cure heat treatment, such as a post-curing cycle. Post thermal treatment typically occurs at a temperature of about 40° C. to about 220° C. In an embodiment, the post thermal treatment is at a temperature of about 60° C. to about 100° C. Typically, the post thermal treatment occurs for a time period of about 5 minutes to about 10 hours, such as about 10 minutes to about 30 minutes, or alternatively about 1 hour to about 4 hours. It will be appreciated that the post thermal treatment temperature and time can be within a range between any of the minimum and maximum values noted above. In an alternative example, the radiation cured article is not subjected to a post thermal treatment. In an example, post processing of the radiation cured article includes shaping, finishing, polishing, trimming, or the like.

Once formed and cured, particular embodiments of the above-disclosed method of forming the radiation curable article advantageously exhibit desired properties such as increased productivity and an improved radiation cured article. In a particular embodiment, the silicone composition and radiation cure of the silicone material can form an article that is not achieved by conventional radiation curable compositions. The radiation source cures the silicone composition to provide a three dimensional article with desirable and in some cases, improved properties compared to a three dimensional printed article formed with a different polymer system. In a particular embodiment, complex three dimensional radiation cured articles may be formed.

Further, particular embodiments of the above-disclosed radiation curable article advantageously exhibit desired properties such as lower extractables and lower volatile organic content than conventional two-part silicone rubber systems that are thermally cured. Further, the radiation curable article has advantageous shear and peel. In particular, the radiation curable article easily releases with a 180° peel and has a high shear force when pulled at a low angle. Further, the radiation curable article has low extractables when extracted by any reasonable solvent, such as for example, hexane, toluene, ethanol, water, and the like.

The radiation curable article is useful for any industry envisioned. Further, although described primarily as a three dimensional article, it is envisioned that the silicone composition can be used for any article, profile, or film. In an embodiment, the radiation curable article may be envisioned for any reasonable medical or industrial application. Exemplary articles include medical devices, medical tubing, adhesives, sealants, foams, and the like. In a particular embodiment, the radiation curable article is an adhesive. For instance, the radiation curable article may be used as an adhesive to any reasonable substrate such as a glass, a metal, a wood, a polymer, or combination thereof. In a particular embodiment, the radiation curable article can be used as a medical device such as a medical wound article, such as a tourniquet or wound dressing.

Many different aspects and embodiments are possible. Some of those aspects and embodiments are described herein. After reading this specification, skilled artisans will appreciate that those aspects and embodiments are only illustrative and do not limit the scope of the present invention. Embodiments may be in accordance with any one or more of the items as listed below.

Embodiment 1

A radiation curable article including a silicone composition including a silicone oligomer and a photoactive catalyst, wherein the silicone oligomer includes at least one alkenyl group and at least one hydride group, the radiation curable silicone oligomer having a viscosity of less than about 100,000 centipoise prior to cure.

Embodiment 2

A method of forming a radiation curable article including providing a silicone composition including a silicone oligomer and a photoactive catalyst, wherein the silicone oligomer includes at least one alkenyl group and at least one hydride group, the silicone oligomer having a viscosity of less than about 100,000 centipoise prior to cure; and irradiating the silicone composition with a radiation source.

Embodiment 3

A radiation curable article including a silicone composition including a silicone oligomer and a photoactive catalyst, wherein the silicone oligomer including at least one alkynyl group and at least one hydride group, the radiation curable silicone oligomer having a viscosity of less than about 100,000 centipoise prior to cure.

Embodiment 4

The radiation curable article or method of forming the radiation curable article of any of the preceding embodiments, wherein the silicone oligomer includes a number of $R_2SiO_{2/2}$ ("D") units, where R is an alkenyl group, an alkynyl group, a hydride group, an alkyl group, an alkoxy group, a phenyl group, a halogenated alkyl group, or combination thereof, the number of D units repeating from less than about 500.

Embodiment 5

The radiation curable article or method of forming the radiation curable article of any of the preceding embodiments, wherein the silicone oligomer has a viscosity of less than about 50,000 prior to cure.

Embodiment 6

The radiation curable article or method of forming the radiation curable article of embodiments 1 or 2, wherein the at least one hydride group and at least one alkenyl group are present in a ratio of about 1:2 to about 2:1.

Embodiment 7

The radiation curable article or method of forming the radiation curable article of embodiments 1 or 2, wherein the at least one hydride group is at a terminal end of the silicone oligomer and the at least one alkenyl group is at an opposite terminal end of the silicone oligomer.

Embodiment 8

The radiation curable article or method of forming the radiation curable article of embodiment 7, wherein at least two hydride groups are at the terminal end of the silicone oligomer and at least two alkenyl groups are at the opposite terminal end of the silicone oligomer.

Embodiment 9

The radiation curable article or method of forming the radiation curable article of embodiments 1 or 2, wherein the at least one hydride group of the silicone oligomer cross-links with at least one alkenyl group of a respective silicone oligomer.

Embodiment 10

The radiation curable article or method of forming the radiation curable article of any of the preceding embodiments, wherein the silicone oligomer is present at an amount of at least about 60 weight %, at least about 70 weight %, at least about 80 weight %, or even at least about 90 weight %, based on the total weight of the silicone composition.

Embodiment 11

The radiation curable article or method of forming the radiation curable article of any of the preceding embodiments, wherein the photoactive catalyst is present at an amount of greater than about 5 ppm, such as about 5 ppm to about 25 ppm, based on the total weight of the silicone composition.

Embodiment 12

The radiation curable article or method of forming the radiation curable article of any of the preceding embodiments, wherein the photoactive catalyst includes a transition metal.

Embodiment 13

The radiation curable article or method of forming the radiation curable article of embodiment 12, wherein the transition metal includes platinum.

Embodiment 14

The radiation curable article or method of forming the radiation curable article of any of the preceding embodiments, wherein the silicone composition further includes a colorant.

Embodiment 15

The radiation curable article or method of forming the radiation curable article of any of the preceding embodiments, wherein the silicone composition further includes a filler.

Embodiment 16

The radiation curable article or method of forming the radiation curable article of embodiment 15, wherein the filler includes an inorganic filler.

Embodiment 17

The radiation curable article or method of forming the radiation curable article of any of the preceding embodiments, wherein the silicone composition further includes a cross-linking agent.

Embodiment 18

The radiation curable article or method of forming the radiation curable article of any of the preceding embodiments, wherein the article is a three dimensional printed radiation cured article.

Embodiment 19

The method of forming the radiation curable article of embodiment 2, wherein the radiation source is ultraviolet energy with a wavelength of about 10 nanometers (nm) to about 410 nm.

Embodiment 20

The method of forming the radiation curable article of embodiment 2, wherein the radiation source substantially cures the silicone composition.

Embodiment 21

The method of forming the radiation curable article of embodiment 2, wherein providing the silicone composition includes depositing the silicone composition upon a print region surface; and successively depositing an additional amount of the silicone composition to form a three dimensional radiation cured article.

Embodiment 22

The method of forming the radiation curable article of embodiment 21, wherein irradiating the silicone composition successively occurs after each of the amounts of the silicone composition have been deposited.

Embodiment 23

The method of forming the radiation curable article of embodiment 2, wherein providing the silicone composition includes filling at least a portion of a container with the silicone composition and irradiating the silicone composition includes selectively irradiating at least a portion of the silicone composition to form a three dimensional radiation cured article.

Embodiment 24

The radiation curable article of embodiment 1, wherein the article is a medical device or an adhesive.

The concepts described herein will be further described in the following examples, which do not limit the scope of the disclosure described in the claims. The following examples are provided to better disclose and teach processes and compositions of the present invention. They are for illustrative purposes only, and it must be acknowledged that minor variations and changes can be made without materially affecting the spirit and scope of the invention as recited in the claims that follow.

EXAMPLES

Example 1

Component A). ExSil™ 100 Part A (Gelest®), contains chemical CAS #104780-63-4 (a poly(dimethylsiloxane) that is terminated with a monohydride and terminated with a monovinyl on opposite ends), with n repeating unit <40. The viscosity of CAS #104780-63-4 is 40-60 centipoise (cPs) at room temperature. The Exsil 100 Part A also contains >30% by weight silica filler and the final viscosity of Exsil 100 Part A is 12,000 to 14,000 cPs at room temperature. The chemical formula of ExSil 100 is:

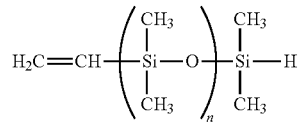

Component B). Trimethyl(methylcyclopentadienyl) platinum (IV) solution in octamethlycyclotetrasiloxane (D4) with Pt concentration of 1000 ppm. The Trimethyl(methylcyclopentadienyl) platinum is a photoactivable catalyst for hydrosilyation.

20 grams of component A and 2 grams of component B are mixed thoroughly. The liquid mixture is then placed in an aluminum pan, 1.5 inches below a LED UV lamp with (300 Watt output) for 10 minutes. The liquid mixture becomes solid elastomer with a hardness about 2 (shore A).

Example 2

A layer of such mixture of component A and B in example 1 is deposited in a desired pattern on a fluoropolymer coated substrate. Three (3) more layers of such mixture are then deposited on the first layer, building a 3D structure. The structure is then placed under a LED UV lamp (300 Watt output), radiated for 10 minutes and a solid three dimensional structure is formed.

Example 3

0.2 grams of Perkadox PD 50S PS, Bis (2,4-dichlorobenzoyl) peroxide 50% paste is dissolved in silicone oil, in 10 ml of Toluene. The use of toluene is to swell a solid elastomer formed as described in example 1 overnight. This also diffuses the perkadox PD 50S PS peroxide into the formed silicone elastomer. The toluene is dissolved until the smell of toluene is undetectable. The peroxide loaded silicone elastomer is placed in an oven at 150° C. for 5 minutes.

The hardness of silicone elastomer is measured after it is taken out of the oven and cooled down to room temperature. The hardness of the silicone elastomer prior to peroxide loading is 2 (Shore A). After peroxide loading, the hardness increased to 7 (Shore A), which is an indication that the peroxide crosslinked the silicone elastomer.

Note that not all of the activities described above in the general description or the examples are required, that a portion of a specific activity may not be required, and that one or more further activities may be performed in addition to those described. Still further, the order in which activities are listed is not necessarily the order in which they are performed.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

The specification and illustrations of the embodiments described herein are intended to provide a general understanding of the structure of the various embodiments. The specification and illustrations are not intended to serve as an exhaustive and comprehensive description of all of the elements and features of apparatus and systems that use the structures or methods described herein. Separate embodiments may also be provided in combination in a single embodiment, and conversely, various features that are, for brevity, described in the context of a single embodiment, may also be provided separately or in any subcombination. Further, reference to values stated in ranges includes each and every value within that range. Many other embodiments may be apparent to skilled artisans only after reading this specification. Other embodiments may be used and derived from the disclosure, such that a structural substitution, logical substitution, or another change may be made without departing from the scope of the disclosure. Accordingly, the disclosure is to be regarded as illustrative rather than restrictive.

What is claimed is:

1. A radiation curable article consists of:
    a silicone composition consisting of a silicone oligomer, a photoactive catalyst, a filler, an optional colorant, and an optional cross-linking agent consisting of a peroxide catalyst, a tin catalyst, or combination thereof, wherein the silicone oligomer comprises at least one alkenyl group and at least one hydride group, wherein the at least one hydride group is at a terminal end of the silicone oligomer and the at least one alkenyl group is at an opposite terminal end of the silicone oligomer, the radiation curable silicone oligomer having a viscosity of less than about 100,000 centipoise prior to cure, wherein the viscosity is measured at about 25° C.; and
    an optional additional layer comprising a material different than the silicone composition.

2. The radiation curable article of claim 1, wherein the silicone oligomer comprises a number of $R_2SiO_{2/2}$ ("D") units, where R is an alkenyl group, an alkynyl group, a hydride group, an alkyl group, an alkoxy group, a phenyl group, a halogenated alkyl group, or combination thereof, the number of D units repeating from less than about 500.

3. The radiation curable article of claim 1, wherein the at least one hydride group and at least one alkenyl group are present in a ratio of about 1:2 to about 2:1.

4. The radiation curable article of claim 1, wherein at least two hydride groups are at the terminal end of the silicone oligomer and at least two alkenyl groups are at the opposite terminal end of the silicone oligomer.

5. The radiation curable article of claim 1, wherein the at least one hydride group of the silicone oligomer cross-links with at least one alkenyl group of a respective silicone oligomer.

6. The radiation curable article of claim 1, wherein the silicone oligomer is present at an amount of at least about 60 weight %, based on the total weight of the silicone composition.

7. The radiation curable article of claim 1, wherein the photoactive catalyst is present at an amount of greater than about 5 ppm, based on the total weight of the silicone composition.

8. The radiation curable article of claim 1, wherein the photoactive catalyst comprises a transition metal.

9. The radiation curable article of claim 1, wherein the cross-linking agent is a peroxide catalyst.

10. The radiation curable article of claim 1, wherein the article is a medical device or an adhesive.

11. A radiation curable article consists of:
    a silicone composition consisting of a silicone oligomer, a photoactive catalyst, a filler, an optional colorant, and an optional cross-linking agent consisting of a peroxide catalyst, a tin catalyst, or combination thereof, wherein the silicone oligomer comprises at least one alkynyl group and at least one hydride group, wherein the at least one hydride group is at a terminal end of the silicone oligomer and the at least one alkynyl group is at an opposite terminal end of the silicone oligomer, the radiation curable silicone oligomer having a viscosity of less than about 100,000 centipoise prior to cure, wherein the viscosity is measured at about 25° C.; and
    an optional additional layer comprising a material different than the silicone composition.

* * * * *